United States Patent [19]

Antos

[11] 4,177,218

[45] * Dec. 4, 1979

[54] DEHYDROGENATION PROCESS UTILIZING MULTIMETALLIC CATALYTIC COMPOSITE

[75] Inventor: George J. Antos, Arlington Heights, Ill.

[73] Assignee: UOP Inc., Des Plaines, Ill.

[ * ] Notice: The portion of the term of this patent subsequent to Jul. 18, 1995, has been disclaimed.

[21] Appl. No.: 912,708

[22] Filed: Jun. 5, 1978

Related U.S. Application Data

[63] Continuation-in-part of Ser. No. 803,693, Jun. 6, 1977, Pat. No. 4,101,418, which is a continuation-in-part of Ser. No. 699,748, Jun. 24, 1976, Pat. No. 4,046,711.

[51] Int. Cl.$^2$ ................................................. C07C 5/36
[52] U.S. Cl. .................................... 585/379; 585/434; 208/139; 585/444; 585/629; 585/660
[58] Field of Search ............ 260/666 A, 683.3, 668 D, 260/669; 208/139

[56] References Cited

U.S. PATENT DOCUMENTS

| | | | |
|---|---|---|---|
| 3,647,719 | 3/1972 | Hayes | 260/683.3 |
| 3,772,213 | 11/1973 | Mitsche | 208/139 |
| 4,101,418 | 7/1978 | Antos | 208/139 |

*Primary Examiner*—Veronica O'Keefe
*Attorney, Agent, or Firm*—James R. Hoatson, Jr.; Robert W. Welch; William H. Page, II

[57] ABSTRACT

A process for the catalytic dehydrogenation of a dehydrogenatable hydrocarbon is disclosed. The hydrocarbon is passed in contact with a germanium-promoted platinum group metal catalyst at dehydrogenation reaction conditions, said catalyst having been prepared by impregnating a porous high surface area carrier material with a non-aqueous solution of a platinum group metal and a halo-substituted germane containing less than about 4 halo substituents, and drying, calcining and reducing the impregnated carrier material.

17 Claims, No Drawings

DEHYDROGENATION PROCESS UTILIZING MULTIMETALLIC CATALYTIC COMPOSITE

CROSS-REFERENCE TO RELATED APPLICATIONS

This application is a continuation-in-part of a copending application Ser. No. 803,693 filed June 6, 1977, and now U.S. Pat. No. 4,101,418, issued July 18, 1978, which is in turn a continuation-in-part application of a copending application Ser. No. 699,748 filed June 24, 1976, now U.S. Pat. No. 4,046,711.

The present invention relates to a process for the catalytic dehydrogenation of a dehydrogenatable hydrocarbon. The process of this invention is particularly useful with respect to the dehydrogenation of ethane, propane, n-butane, isobutane, n-pentane, isopentane, and the like. The process of this invention is also advantageously applied to effect the dehydrogenation of various other paraffinic hydrocarbons containing 6 or more carbon atoms per molecule. The dehydrogenation products find extensive use in a variety of industries including the petroleum, petrochemical, pharmaceutical and plastic industries. For example, propylene is used in the manufacture of isopropyl alcohol, cumene, polypropylene and polypropylene dimer, trimer, and tetramer, and in the synthesis of isoprene; butylene, including butene-1 and cis and trans butene-2 is extensively employed in polymer and alkylate gasolines, in the manufacture of polybutene, butadiene, aldehydes and alcohols, and as polymer cross-linking agents; isobutene finds use in the production of isooctane, butyl rubber and acrylonitrile; and substantially straight-chain monoolefins in the $C_{10}$–$C_{20}$ range are important alkylating agents in the manufacture of certain alkylbenzenes, the sulfonated derivatives of which are desirable biodegradable detergents.

It is an object of this invention to present an improved catalytic dehydrogenation process utilizing a dehydrogenation catalyst comprising a platinum group metal component and a germanium component and characterized by a novel method of preparation.

In one of its broad aspects, the present invention embodies a process for the catalytic dehydrogenation of a dehydrogenatable hydrocarbon which comprises passing said hydrocarbon in contact with a germanium-promoted platinum group metal catalyst at dehydrogenation reaction conditions, said catalyst having been prepared by impregnating a porous high surface area carrier material with a non-aqueous solution of a platinum group metal compound and a halo-substituted germane containing less than 4 halo substituents in an amount to provide a final catalyst containing from about 0.05 to about 1.0 wt. % platinum group metal and from about 0.05 to about 1.0 wt. % germanium, and drying, calcining and reducing the thus impregnated carrier material.

One of the more specific embodiments is in a process for the catalytic dehydrogenation of a paraffinic hydrocarbon which comprises passing said hydrocarbon in contact with a germanium-promoted platinum catalyst in admixture with hydrogen and in admixture with from about 50 to about 10,000 parts per million water at dehydrogenation reaction conditions including a liquid hourly space velocity of from about 1 to about 40, a temperature of from about 375° to about 650° C., a pressure of from about 0.1 to about 10 atmospheres, and a hydrogen/hydrocarbon mole ratio of from about 1:1 to about 20:1, said catalyst having been prepared by impregnating a porous high surface area carrier material with a common alcoholic solution of chloroplatinic acid and trichlorogermane in an amount to provide a final catalyst containing from about 0.05 to about 1.0 wt. % platinum and from about 0.05 to about 1.0 wt. % germanium, and drying, calcining and reducing the impregnated carrier material.

A still more specific embodiment concerns a process which comprises passing a substantially straight chain paraffinic hydrocarbon, containing from about 6 to about 30 carbon atoms; in contact with a germanium-promoted platinum catalyst in admixture with hydrogen and in admixture with from about 1500 to about 5000 parts per million water at dehydrogenation reaction conditions including a liquid hourly space velocity of from about 25 to about 35, a temperature of from about 375° to about 550° C., a pressure of from about 0.5 to about 3 atmospheres, and a hydrogen/hydrocarbon mole ratio of from about 1.5:1 to about 10:1, said catalyst having been prepared by impregnating a porous high surface area alumina with a common alcoholic solution of chloroplatinic acid and trichlorogermane in an amount to provide a final catalyst containing from about 0.05 to about 1.0 wt. % platinum and from about 0.05 to about 1.0 wt. % germanium, and drying, calcining and reducing the impregnated alumina at a temperature of from about 425° to about 760° C.

Other objects and embodiments of this invention will become apparent in the following detailed specification.

Dehydrogenatable hydrocarbons subject to the dehydrogenation process of this invention are such as have heretofore been treated at dehydrogenation reaction conditions to yield a product of reduced saturation. Said hydrocarbons include partially saturated hydrocarbons like butene, pentene, hexene, cyclopentene, cyclohexene, etc., which can be dehydrogenated to form polyunsaturated products such as butadiene, pentadiene, hexadiene, cyclopentadiene, cyclohexadiene, benzene and the like. More particularly, suitable dehydrogenatable hydrocarbons include aliphatic and cyclic paraffins containing from about 2 to about 30 carbon atoms per molecule. Specific examples include the aliphatic paraffins ethane, propane, n-butane, isobutane, n-pentane, isopentane, n-hexane, 2-methylpentane, 2,2-dimethylpentane, as well as the normal and isomeric heptanes, octanes, nonanes, decanes, and the like containing up to about 30 carbon atoms per molecule. Dehydrogenatable cycloparaffins, or naphthenes, include cyclopentane, methylcyclopentane, ethylcyclopentane, n-propylcyclopentane, isopropylcyclopentane, cyclohexane, 1,3-dimethylcyclohexane, and the like. The dehydrogenatable hydrocarbons also include the alkyl aromatic hydrocarbons such as ethylbenzene, n-propylbenzene, isopropylbenzene, and the like.

In the preparation of the dehyrogenation catalyst of this invention, a halo-substituted germane and a platinum group metal compound are prepared in a common non-aqueous solution to deposit a germanium component and a platinum group metal component on a high surface area carrier material. The platinum group metal component is preferably platinum although rhodium, ruthenium, osmium, iridium, and particularly palladium are suitable components. The non-aqueous solution is suitably an absolute alcohol solution, absolute ethanol being preferred. Platinum group metal compounds for use in said non-aqueous solution include chloroplatinic acid, platinum chloride, ammonium chloroplatinate, dinitrodiamino-platinum, palladium chloride, chloropalladic acid, rhodium chloride, ruthenium chloride, ruthenium oxide, osmium chloride, iridium chloride, chloroiridic acid, and the like. Chloroplatinic acid is a preferred platinum group metal compound for use herein. In any case, the selected platinum group metal compound is utilized in an amount to provide a catalyst product containing from about 0.05 to about 1.0 wt. % platinum group metal.

The halo-substituted germanes herein contemplated are those containing less than four halo substituents. Preferably, the halo-substituted germane prepared in common solution with the platinum group metal compound is a chlorogermane, that is, chlorogermane, dichlorogermane, or trichlorogermane. Other suitable halo-substituted germanes include the corresponding fluoro-, bromo-, and iodo-substituted germanes, in particular, the normally liquid bromogermane, dibromogermane, tribromogermane and the like. The selected halo-substituted germane is preferably employed in an amount to provide a catalyst product containing from about 0.05 to about 1.0 wt. % germanium. In one preferred embodiment, the halo-substituted germane is trichlorogermane.

The improvement in catalytic activity stability observed in the practice of this invention is believed to result from the formation of a complex of the halo-substituted germane with the platinum group metal compound whereby the germanium and platinum group metal components are deposited and distributed on the surface of the carrier material in intimate association to more fully realize the synergistic potential of said components heretofore observed with respect to the catalytic conversion of hydrocarbons.

Pursuant to the method of the present invention, a high surface area, porous carrier material is impregnated with the described non-aqueous impregnating solution. Suitable carrier materials include any of the various and well-known solid adsorbent materials generally utilized as a catalyst support or carrier material. Said adsorbent materials include the various charcoals produced by the destructive distillation of wood, peat, lignite, nutshells, bones, and other carbonaceous matter and preferably such charcoals as have been heat treated, or chemically treated, or both, to form a highly porous particle structure of increased adsorbent capacity, and generally defined as activated carbon. Said adsorbent materials also include the naturally occurring clays and silicates, for example, diatomaceous earth, fuller's earth, kieselguhr, attapulgus clay, feldspar, montmorillonite, halloysite, kaolin and the like, and also the naturally occurring or synthetically prepared refractory inorganic oxides such as alumina, silica, zirconia, thoria, boria, etc., or combinations thereof like silica-alumina, silica-zirconia, alumina-zirconia, etc. The preferred porous carrier materials for use in the present invention are the refractory inorganic oxides with best results being obtained with an alumina carrier material. It is preferred to employ a porous, adsorptive, high surface are material characterized by a surface area of from about 25 to about 500 m²/gm. Suitable aluminas thus include gamma-alumina, eta-alumina, and theta-alumina, with the first mentioned gamma-alumina being preferred. A particularly preferred alumina is gamma-alumina characterized by an apparent bulk density of from about 0.30 to about 0.90 gms. per cubic centimeter, an average pore diameter of from about 50 to about 150 Angstroms, an average pore volume of from about 0.10 to about 1.0 cubic centimeters per gram, and a surface area of from about 150 to about 500 square meters per gram.

The alumina employed may be a naturally occurring alumina or it may be synthetically prepared in any conventional or otherwise convenient manner. The alumina is typically employed in a shape or form determinative of the shape or form of the final catalyst composition, e.g., spheres, pills, granules, extrudates, powder, etc. A particularly preferred form of alumina is the sphere, especially alumina spheres prepared substantially in accordance with the oil-drop method described in U.S. Pat. No. 2,620,314. Briefly, said method comprises dispersing droplets of an alumina sol in a hot oil bath. The droplets are retained in the oil bath until they set into firm gel spheroids. The spheroids are continuously separated from the bath and subjected to specific aging treatments to promote certain desirable properties. The spheres are subsequently dried at from about 40° to about 200° C. and thereafter calcined at from about 425° to about 760° C. As an aid in reducing the acid anion content of the final catalyst to an acceptable level, the calcination may be effected in the presence of steam, for example, the calcination may be effected in air containing up to about 25% steam.

Impregnating conditions employed herein involve conventional impregnating techniques known to the art. Thus, the catalytic component, or soluble compound thereof, is adsorbed on the carrier material by soaking, dipping, suspending, or otherwise immersing the carrier material in the impregnating solution, suitably at ambient temperature conditions. The carrier material is preferably maintained in contact with the impregnating solution at ambient temperature conditions for a brief period, preferably for at least about 30 minutes, and the impregnating solution thereafter evaporated substantially to dryness at an elevated temperature. For example, a volume of alumina particles is immersed in a substantially equal volume of impregnating solution in a steam-jacketed rotary dryer and tumbled therein for a brief period at about room temperature. Thereafter, steam is applied to the jacket of the dryer to expedite the evaporation of said solution and the recovery of substantially dry impregnated carrier material.

It is a preferred practice to further impregnate the supported germanium-promoted platinum group metal dehydrogenation catalyst with an alkali metal or alkaline earth metal component to suppress the acidic character of the catalyst resulting, for example, from the preferred acidic impregnation of the germanium and platinum group metal components. The alkali metal component, i.e., sodium, potassium, lithium, cesium and rubidium, and the alkaline earth metal component, i.e., calcium, strontium, barium and magnesium, are suitably impregnated from an aqueous solution of a soluble salt thereof, the nitrates being especially useful. In any case, the alkali metal or alkaline earth metal component will suitably comprise from about 0.1 to about 5 wt. % of the dehydrogenation catalyst. The alkali metal or alkaline earth metal component, preferably lithium or potassium, can be impregnated on the support or carrier material before, during or subsequent to its calcination, or before, during or subsequent to impregnation of the support or carrier material with the germanium and platinum group metal components. It is considered that the better results are obtained when the alkali metal or alkaline earth metal component is added to subsequent to the germanium and platinum group metal components whereby the residual acidity resulting from the preferred acidic impregnating conditions is substantially neutralized.

Regardless of the details of how the components of the catalyst are combined with the porous carrier material, the final catalyst composite generally will be calcined in an oxidizing atmosphere, such as air, at a temperature of from about 200° to about 650° C. The catalyst particles are advantageously calcined in stages to experience a minimum of breakage. Thus, the catalyst particles are advantageously calcined for a period of from about 1 to about 3 hours in an air atmosphere at a temperature of from about 200° to about 375° C., and immediately thereafter at a temperature of from about 475° to about 650° C. in an air atmosphere for a period of from about 3 to about 5 hours. Again, as an aid in reducing the acid anion content of the catalyst to an acceptable level, the calcination may be effected in air comprising up to about 25% steam.

It is preferred that the resultant calcined catalytic composite is subjected to a substantially water-free reduction step prior to its use in the conversion of hydrocarbons. This step is designed to further insure a uniform and finely divided dispersion of the metallic components throughout the carrier material. Preferably, substantially pure and dry hydrogen (i.e., less than 20 volume ppm. $H_2O$) is used as the reducing agent in this step. The reducing agent is contacted with the oxidized catalyst at conditions including a temperature of from about 800° to about 1200° F. This reduction step may be performed in situ as a part of a start-up sequence if precautions are taken to predry the plant to a substantially water-free state, and if substantially water-free hydrogen is used. The duration of this step is preferably less than 2 hours, and more typically about 1 hour.

The dehydrogenatable hydrocarbon is generally passed in contact with the described catalyst in admixture with hydrogen to suppress the formation of hydrogen-deficient carbonaceous matter on the catalyst, and to lower the partial pressure of the dehydrogenatable hydrocarbon. Sufficient hydrogen is generally charged to provide a hydrogen/hydrocarbon mole ratio in contact with a catalyst of from about 1:1 to about 20:1, and preferably from about 1.5:1 to about 10:1. The hydrogen admixed with the dehydrogenatable hydrocarbon is typically recycle hydrogen recovered from the dehydrogenation reactor effluent. The dehydrogenatable hydrocarbon is further advantageously admixed with water, or a water generating substance such as a $C_2$-$C_8$ alcohol, ether, ketone, aldehyde, or a like oxygen-containing compound decomposable to water at dehydrogenation reaction conditions. The water can be charged to the dehydrogenation reactor independently, admixed with the hydrocarbon, or admixed with the hydrogen. It is generally preferred to inject the water by saturating at least a portion of the hydrogen with water, the saturated hydrogen being subsequently admixed with the dehydrogenatable hydrocarbon passed in contact with the catalyst. In any case, sufficient water should be admixed with the dehydrogenatable hydrocarbon to provide from about 50 to about 10,000 wt. ppm. in contact with the catalyst, and preferably from about 1500 to about 5,000 wt. ppm.

The dehydrogenation reaction conditions herein contemplated are substantially as described in the art to effect the catalytic dehydrogenation of a given dehydrogenatable hydrocarbon. In general, the dehydrogenation temperature will be from about 375° to about 650° C., a temperature in the lower range being suitably effective for the more readily dehydrogenated hydrocarbons, such as the higher molecular weight, substantially straight chain paraffins, and a temperature in the upper range being more effective with respect to the more difficultly dehydrogenated lower molecular weight hydrocarbons, such as ethane, propane, butane, and the like. For example, for the dehydrogenation of $C_6$-$C_{30}$ substantially straight chain paraffins, best results are generally achieved at a temperature of from about 375° to about 550° C. Dehydrogenation reaction conditions further include a pressure of from about 0.1 to about 10 atmospheres. It is the general practice to select the lowest pressure consistent with catalyst stability. Thus, the pressure is preferably in the range of from about 0.1 to about 3 atmospheres. The dehydrogenatable hydrocarbon is suitably maintained in contact with the catalyst at dehydrogenation conditions for a time equivalent to a liquid hourly space velocity of from about 1 to about 40, with the best results being obtained at a liquid hourly space velocity of from about 25 to about 35 for the dehydrogenation of the relatively high molecular weight, substantially straight chain paraffins.

The following examples are presented in illustration of the process of this invention and are not intended as an undue limitation on the generally broad scope of the invention as set out in the appended claims.

EXAMPLE I

Gamma-alumina spheres of about 1/16" diameter were prepared by the described oil-drop method. Thus, an aluminum chloride hydrosol, prepared by digesting aluminum pellets in dilute hydrochloric acid, was commingled with hexamethylenetetramine and dispersed as droplets in a hot oil bath. The resulting spheres were aged in the oil bath overnight and then washed, dried and calcined. The alumina spheres had an average bulk density of about 0.5 gms/cc and a surface area of about 180 m²/gms.

In preparing the impregnating solution, trichlorogermane and chloroplatinic acid were dissolved in absolute ethanol to form a common solution thereof. The solution was stabilized with a quantity of $HNO_3$ equivalent to about 3 wt. % of the alumina to be impregnated. The solution was thereafter diluted to about 300 cc.

About 350 cc of the calcined alumina spheres were immersed in the impregnating solution in a steam-jacketed rotary evaporator, the volume of the impregnating solution being substantially equivalent to the volume of the carrier material. The spheres were allowed to soak in the rotating evaporator for about 30 minutes at room temperature and steam was thereafter applied to the evaporator jacket. The solution was evaporated substantially to dryness, and the dried spheres were subsequently dried in air for about 1 hour at 150° C. and immediately thereafter calcined in air containing 3% $H_2O$ for about 2 hours at 525° C. The resultant oxidized catalyst particles were reimpregnated with an aqueous lithium nitrate solution and dried. The oxidized catalyst is calcined in dry air for about 2 hours at 525° C. The catalyst particles were then treated in a substantially pure hydrogen stream containing less than 20 vol. ppm. $H_2O$ for about 1 hour at 565° C. to yield the reduced form of the catalyst. The final catalyst product contained 0.375 wt. % platinum, 0.25 wt. % germanium and 0.6% lithium calculated as the elemental metal.

In a continuous process for the dehydrogenation of n-hexane representing one preferred embodiment of this invention, the described catalyst is disposed as a fixed bed in a vertical tubular reactor equipped with a preheater and suitable heating means whereby the reactant stream is preheated to about 510° and maintained at about this temperature in contact with the catalyst bed. A commercial grade of n-hexane is charged to the reactor by means of a compressor at a rate to effect a liquid hourly space velocity of about 30. The n-hexane is admixed with a water-saturated, hydrogen-rich recycle gas to effect a recycle gas/hydrocarbon mole ratio of about 5.1, and the mixture is processed downwardly through the catalyst bed at said liquid hourly space velocity of about 30. The reactor outlet pressure is controlled at about 20 psig. The reactor effluent stream is passed to a high pressure-low temperature separator wherein the reactor effluent is cooled and separated into a liquid phase and a gaseous phase. A portion of the hydrogen-rich gaseous phase is continuously withdrawn overhead from the separator and recycled to provide the aforementioned recycle gas/hydrocarbon mole ratio charged to the reactor. The liquid phase is continuously withdrawn from the separator through a pressure reducing valve. After a lineout period, a 20 hour test period is conducted during which the average conversion of the n-hexane is 12% at a selectivity for n-hexene of 90%.

EXAMPLE II

In the dehydrogenation of a commercial grade of n-dodecane to effect in excess of 90% selectivity to n-dodecene, the dodecane is processed substantially as shown in the previous example. However, in this instance the dedecane is admixed with the water-saturated, hydrogen-rich recycle gas to effect a recycle gas/hydrocarbon mole ratio of about 8:1, and the process downwardly through the catalyst bed at a liquid hourly space velocity of approximately 32 while maintaining the reactant stream at a temperature of about 465° C., and the reactor outlet pressure at about 10 psig.

I claim as my invention:

1. A process for the catalytic dehydrogenation of a dehydrogenatable hydrocarbon which comprises passing said hydrocarbon in contact with a germanium-promoted platinum group metal catalyst at a liquid hourly space velocity of from about 1 to about 40, a temperature of from about 375° to about 650° C., a pressure of from about 0.1 to about 10 atmospheres, and a hydrogen/hyrocarbon mole ratio of from about 1:1 to about 20:1, said catalyst having been prepared by impregnating a porous high surface area carrier material with a non-aqueous solution of a platinum group metal compound and a halo-substituted germane selected from the group consisting of chloro-, fluoro-, bromo-, and iodo-substituted germanes containing less than 4 halo substituents in an amount to provide a final catalyst containing from about 0.05 to about 1.0 wt. % platinum group metal and from about 0.05 to about 1.0 wt. % germanium, and drying, calcining and reducing the thus impregnated carrier material.

2. The process of claim 1 further characterized in that said soluble platinum group metal compound is a platinum compound.

3. The process of claim 1 further characterized in that said soluble platinum group metal compound is chloroplatinic acid.

4. The process of claim 1 further characterized in that said halo-substituted germane is a chloro-substituted germane.

5. The process of claim 1 further characterized in that said halo-substituted germane is trichlorogermane.

6. The process of claim 1 further characterized in that said non-aqueous solution is an alcoholic solution.

7. The process of claim 1 further characterized in that said carrier material is a refractory inorganic oxide.

8. The process of claim 1 further characterized in that said carrier material is an alumina carrier material.

9. The process of claim 1 further characterized in that said impregnated carrier material is dried and calcined at a temperature of from about 425° to about 760° C.

10. The process of claim 1 further characterized in that said germanium-promoted platinum group metal catalyst further contains from about 0.1 to about 5 wt. % alkali metal or alkaline earth metal impregnated thereon.

11. The process of claim 1 further characterized in that said germanium-promoted platinum group metal catalyst further contains from about 0.1 to about 5 wt. % lithium impregnated thereon.

12. The process of claim 1 further characterized in that said germanium-promoted platinum group metal catalyst further contains from about 0.1 to about 5 wt. % potassium impregnated thereon.

13. The process of claim 1 further characterized in that said dehydrogenatable hydrocarbon is passed in contact with said catalyst in admixture with hydrogen.

14. The process of claim 1 further characterized in that said dehydrogenatable hydrocarbon is passed in contact with said catalyst in admixture with from about 50 to about 10,000 ppm. water.

15. The process of claim 1 further characterized in that said dehydrogenatable hydrocarbon is an alkyl aromatic hydrocarbon wherein the alkyl substituent contains from about 2 to about 6 carbon atoms.

16. The process of claim 1 further characterized in that said dehydrogenatable hydrocarbon is an aliphatic paraffinic hydrocarbon.

17. The process of claim 1 further characterized in that said dehydrogenatable hydrocarbon is a cycloparaffinic hydrocarbon.

* * * * *